United States Patent [19]
Maekawa et al.

[11] Patent Number: 4,465,867
[45] Date of Patent: Aug. 14, 1984

[54] PROCESS FOR PREPARING O-METHALLYLOXYPHENOL

[75] Inventors: Tsukasa Maekawa; Takeshi Gondo; Shigeo Takahashi; Hidetoshi Kume, all of Tokushima, Japan

[73] Assignee: Otsuka Kagaku Yakuhin Kabushiki Kaisha, Japan

[21] Appl. No.: 387,601

[22] Filed: Jun. 11, 1982

[30] Foreign Application Priority Data

Apr. 7, 1982 [JP] Japan .................................. 57/58744

[51] Int. Cl.³ .............................................. C07C 41/16
[52] U.S. Cl. ..................................... 568/652; 570/235
[58] Field of Search ......................... 568/652; 570/235

[56] References Cited

U.S. PATENT DOCUMENTS 3,474,171 10/1969 Scharpf .............................. 424/285
3,624,168 11/1971 Pawloski ......................... 570/235 X Primary Examiner—Bernard Helfin
Attorney, Agent, or Firm—Larson & Taylor

[57] ABSTRACT

A process for preparing o-methallyloxyphenol by reacting catechol with methallyl chloride in the presence of at least one of KI and NaI serving as a catalyst with use of a base, and an organic solvent or a mixture of an organic solvent and water, the process being characterized in that methallyl chloride is reacted with the catalyst after the reaction to recover the catalyst as converted to methallyl iodide and reuse the catalyst.

6 Claims, No Drawings

PROCESS FOR PREPARING O-METHALLYLOXYPHENOL

This invention relates to a process for preparing o-methallyloxyphenol from catechol and methallyl chloride, and more particularly to the use of a catalyst in the process in circulation.

o-Methallyloxyphenol is a known compound useful as a material for carbofuran insecticidal compositions. It is known that when subjected to a rearrangement and cyclization reaction, the compound gives 2,3-dihydro-2,2-dimethyl-7-hydroxybenzofuran useful as a material for preparing agricultural chemicals.

o-Methallyloxyphenol (hereinafter referred to as "monoether") is prepared usually by reacting equimolar amounts of catechol and methallyl chloride in dry acetone in the presence of $K_2CO_3$ and KI under reflux for 30 hours (Published Examined Japanese Patent Publication No. 12263/1967, U.S. Pat. No. 3,474,171). However, these publications suggest nothing about how to recover the KI from the reaction mixture for reuse. Although it is possible to recover the KI, which is expensive, from the reaction mixture containing KCl, unreacted $K_2CO_3$, etc. by concentration and utilizing the difference of solubility in water, this method requires much energy for concentrating water and an intricate procedure, for example, for the separation of crystals and is nevertheless low in recovery efficiency, failing to completely recover the KI.

How to recover the expensive catalyst economically and easily is critical in practicing the above process on an industrial scale.

The object of the present invention is to provide a process for preparing the monoether in which the catalyst can be recovered for use easily and economically, the process further permitting recovery and reuse of other unreacted materials with ease.

The present invention is most distinctly characterized in that after the reaction for preparing the monoether, the catalyst is reacted with methallyl chloride and thereby converted to methallyl iodide for recovery and reuse, whereby the expensive catalyst can be recovered for reuse in circulation economically and easily with reduced energy consumption. This method is very useful for the commercial production of the monoether.

Our research has revealed that the overall monoetherifying reaction including the recovery reaction proceeds according to the following equations (1) and (2), giving the monoether economically in good yield with high reactivity.

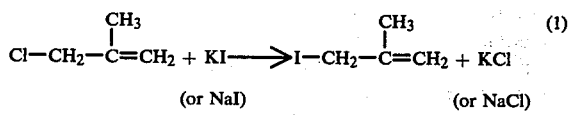

Although the reaction proceeds even in the absence of the catalyst, the reactivity is then very low, such that the reaction, even if conducted for a prolonged period of time, is unable to achieve a high yield as checked before or after the unreacted materials are used up. In the presence of the catalyst, methallyl chloride reacts with the catalyst and is thereby converted, as represented by Equation (1), to highly reactive methallyl iodide, which subsequently reacts with catechol to afford the monoether and the catalyst as represented by Equation (2). Consequently the desired monoether can be obtained in a high yield even if the catalyst is used in a small amount. Further when methallyl iodide is used in place of methallyl chloride in the absence of the catalyst, a similarly high yield is attained. In this case also, however, there arises the problem of how to recover from the reaction mixture the expensive catalyst which is formed as represented by Equation (2) in a large quantity.

According to the invention, methallyl chloride is reacted, as represented by Equation (1), with the reaction mixture containing the catalyst and large amounts of unreacted carbonate, bicarbonate, etc. in the form of crystals or an aqueous solution to convert the catalyst to methallyl iodide for the recovery and reuse. The methallyl chloride reacts with the catalyst selectively and quantitatively without reacting with other compounds, so that the procedure is very simple to carry out.

Stated specifically the catalyst is recovered by the following treatment.

(A) At least one of a precipitate containing the catalyst, an aqueous layer containing the catalyst and aqueous washings containing the catalyst is separated from the reaction mixture by at least one of the procedures of filtration, separation, addition of water and, when desired, washing of the precipitate or the organic layer with water.

When the monoetherifying reaction is conducted using an organic solvent singly, the catalyst is contained in the resulting precipitate. The precipitate is filtered off and then treated as it is, or the separated precipitate may be made into an aqueous solution for the subsequent treatment. Alternatively, instead of filtering the precipitate, water is added to the reaction mixture to dissolve the precipitate to obtain an aqueous layer containing the catalyst for the subsequent treatment. When the organic solvent has the catalyst therein, the whole amount of the catalyst can be transferred to water by washing the organic layer with water. The aqueous washings are then subjected to the next treatment.

When the monoetherifying reaction is conducted in a mixture of an organic solvent and water, the resulting aqueous layer is subjected to the subsequent treatment. The reaction mixture, if containing a precipitate, may be treated in the same manner as when the reaction is conducted with use of an organic solvent only. When the oil layer contains methallyl iodide and distilled in a vacuum, the methallyl iodide becomes incorporated into the resulting fraction, which is therefore subsequently subjected to treatment B or used for the monoetherifying reaction.

(B) Methallyl chloride, or methallyl chloride and an organic solvent, or methallyl chloride, water and an organic solvent are added to the precipitate containing the catalyst, the aqueous layer containing the catalyst or the aqueous washings containing the catalyst, and the mixture is heated to about 0° to about 100° C. to convert the catalyst to methallyl iodide. Thus the precipitate, aqueous layer or aqueous washings resulting from the treatment A and containing the catalyst are reacted with methallyl chloride according to Equation (1) to convert the catalyst to methallyl iodide. Although the reaction of Equation (1) proceeds also in the absence of an organic solvent or water, it is preferable to carry out the reaction in the presence of an organic solvent which dissolves part of the catalyst and methallyl chloride, or in the presence of water and an organic solvent which dissolve solid materials because the reaction system is then easier to handle and exhibits higher reactivity. The reaction temperature, which is not particularly limited, is usually about 0° to about 100° C., preferably about 30° to about 60° C., in view of the reactivity and yield. The reaction time, which is not limited either, is usually 30 minutes to 4 hours, during which the reaction proceeds quantitatively to produce a satisfactory result. The methallyl chloride is used preferably in an amount of at least one mole per mole of the catalyst, and the amount is determined as desired in this range.

(C) The methallyl iodide is used, as contained in an oil layer or separated therefrom, for the reaction for preparing the monoether.

The methallyl iodide obtained according to Equation (1) forms an oil layer. If the amounts of the catalyst and methallyl chloride used are small, the oil layer is in a small amount and difficult to separate off, so that the reaction may be conducted in the presence of an organic solvent, or the reaction mixture may be subjected to extraction with an organic solvent. The oil layer or the organic solvent layer (extract) is usable as it is for the monoetherifying reaction, or the methallyl iodide recovered from the layer, for example, by distillation is used for the reaction. Since the organic solvent and the excess of methallyl chloride are useful as materials for the monoetherifying reaction, it is preferable to use the oil layer or organic solvent layer as it is for the reaction.

When the monoetherifying reaction has not proceeded fully, methallyl iodide remains in the organic solvent, and the amount of the catalyst is smaller by an amount corresponding to the molar amount of the remaining iodide. in this case, the methallyl iodide can be recovered when the organic solvent is recovered, consequently eliminating the loss of the catalyst.

Although solvents other than ketones and aliphatic esters are useable for extracting methallyl iodide, such a solvent, if used, must be removed before the monoetherifying reaction, so that it is desirable to use ketones or aliphatic esters.

The organic solvents useful for the monoetherifying reaction of this invention are ketones represented by the formula $$R^1COR^2$$

wherein $R^1$ and $R^2$ are each alkyl having 1 to 6 carbon atoms or phenyl, or are joined together to form alkylene having 4 to 8 carbon atoms, and aliphatic esters represented by the formula $$R^3COOR^4$$

wherein $R^3$ is hydrogen or alkyl having 1 to 8 carbon atoms, and $R^4$ is alkyl having 1 to 5 carbon atoms. Examples of useful ketones are acetone, methyl ethyl ketone, methyl isobutyl ketone, cyclohexanone, etc. Examples of useful aliphatic esters are methyl formate, ethyl acetate, amyl propionate, amyl valerate, ethyl pelargonate, etc.

The bases useful for the present reaction include carbonates, bicarbonates and hydroxides of alkali metals or alkaline earth metals, cyclic amidines represented by the formula

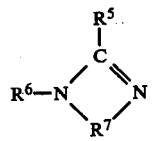

wherein $R^5$ and $R^6$ are each hydrogen or alkyl having 1 to 5 carbon atoms, or are joined together to form alkylene having 2 to 11 carbon atoms, and $R^7$ is alkylene having 2 to 6 carbon atoms, and amines represented by the formula

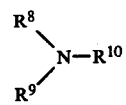

wherein $R^8$ and $R^9$ are each hydrogen, alkyl having 1 to 8 carbon atoms or cycloalkyl having 5 to 8 carbon atoms, or are joined together to form alkylene having 5 to 8 carbon atoms, and $R^{10}$ is hydrogen, alkyl having 1 to 8 carbon atoms or phenyl. These bases are usable singly, or at least two of them are usable in admixture.

Exemplary of useful carbonates, bicarbonates and hydroxides of alkali metals or alkaline earth metals are $K_2CO_3$, $Na_2CO_3$, $KHCO_3$, $NaHCO_3$, $KOH$, $NaOH$, $CaCO_3$, $MgCO_3$, $Ca(OH)_2$, $Mg(OH)_2$, etc.

Examples of useful cyclic amidines are 1,8-diaza-bicyclo[5,4,0]-7-undecene (DBU), 1,6-diaza-bicyclo[4,3,0]-5-nonene, 1,5-diaza-bicyclo[4,2,0]-5-octene, 1,4-diaza-bicyclo[3,3,0]-4-octene, 3-methyl-1,4-diaza-bicyclo[3,3,0]-4-octene, etc.

Examples of useful amines are methylamine, dimethylamine, trimethylamine, ethylamine, diethylamine, triethylamine, cyclohexylamine, dicyclohexylamine, piperidine, etc.

Expensive KI or NaI can be recovered by the present process described above selectively and quantitatively by simple procedures for use in circulation without necessitating any special reagent or apparatus except the materials used for the monoetherifying reaction. Thus the process has great advantages.

For a better understanding of the invention, examples are given below.

Example 1

(1) Monoetherification

In a 200-ml glass reactor equipped with a thermometer, stirrer and reflux condenser, 10 g (91 mM) of catechol was dissolved in 32 g of cyclohexanone saturated with water. To the mixture were added 6.21 g (45 mM) of potassium carbonate and 7.47 g (45 mM) of potassium iodide with stirring, and nitrogen gas was introduced to replace the air in the reactor. The mixture was heated to 90° C., and 8.24 g (91 mM) of methallyl chloride was added dropwise over a period of 10 minutes. The reaction was continued for 15 hours at the same temperature, giving 12.69 g (77.35 mM) of the monoether which corresponded to 85% yield based on the methallyl chloride used.

(2) Treatment A

To the reaction mixture obtained from the above treatment (1) was added 20 g of water to dissolve the precipitate. The resulting solution was separated into oil and water layers. Methallyl iodide was found in an amount of 0.236 g (1.3 mM) in a fraction obtained by the distillation of the oil layer at a reduced pressure. The methallyl iodide was identified by comparing the product with an authentic substance in respect of mass spectrum. No methallyl chloride was found. The water layer contained 7.25 g (43.7 mM) of potassium iodide.

(3) Treatment B

Into the same reactor as used in the above step (1) were placed the water layer and the fractions obtained in the above step (2). To the mixture was added 8.12 g (89.7 mM) of methallyl chloride at 50° C. over a period of 10 minutes with stirring, and the reaction was continued for 20 minutes at the same temperature.

(4) Treatment C

The reaction mixture obtained from the above step (3) was separated into oil and water layers. The oil layer was found to contain 8.15 g (44.8 mM) of methallyl iodide dissolved therein. Iodine was recovered 99.6% in the form of methallyl iodide from the potassium iodide initially used. The oil layer was used for the second monoetherification.

(5) Monoetherification by use of the recovered catalyst

Into the same reactor as used above for monoetherification were placed the oil layer of treatment C, 10 g (91 mM) of catechol and 6.21 g (45 mM) of potassium carbonate, and the air in the reactor was replaced by nitrogen. The mixture was heated to 90° C. over a period of 10 minutes and maintained at the same temperature for 15 hours. Analysis of the reaction mixture showed the formation of 12.8 g (78.0 mM) of the monoether which corresponded to 86% yield based on methallyl halide (i.e., based on the total molar amount of methallyl iodide in treatment A and methallyl chloride in treatment B, the same as hereinafter).

Monoetherification reaction was repeated with the catalyst recovered by the above treatments A, B and C. The results were given in Table 1.

TABLE 1

| No. | Iodine Recovery (%) | Monoether Yield (%) |
|---|---|---|
| 1 | 99.6 | 85 |
| 2 | 98.2 | 86 |
| 3 | 97.4 | 84 |
| 4 | 98.1 | 84 |
| 5 | 99.2 | 83 |
| 6 | 97.0 | 87 |
| 7 | 98.5 | 85 |

Example 2

(1) Monoetherification

Into the same reactor as used in Example 1 were placed 10 g (91 mM) of catechol, 10 g of water and 20 g of methyl ethyl ketone. To the mixture were added 6.21 g (45 mM) of potassium carbonate and 3.65 g (22 mM) of potassium iodide with stirring, and nitogen gas was introduced to replace the air in the reactor. The mixture was heated to reflux temperature, and 8.24 g (91 mM) of methallyl chloride was added dropwise over a period of 10 minutes. The reaction was continued for 10 hours, giving the monoether in a yield of 76% based on the methallyl chloride used.

(2) Treatment A

After completion of the monoetherification, 20 g of water was added to the reaction mixture. The resulting solution was separated into oil and water layers. The oil layer was washed with 5 g of water, and the resulting water layer was mixed with the above water layer. The combined water layer had dissolved therein 3.15 g (19 mM) of potassium iodide. Methallyl iodide was found in an amount of 0.53 g (2.9 mM) in a fraction obtained by the distillation of the oil layer at a reduced pressure. No methallyl chloride was found.

(3) Treatment B

Into the same reactor as used in the above monoetherification were placed the water layer and the fractions obtained in the above step (2). To the mixture was added 7.97 g (88.1 mM) of methallyl chloride, and the reaction was continued for 2 hours at 40° C.

(4) Treatment C

The reaction mixture obtained from the above step (3) was separated into oil and water layers. The oil layer contained 3.94 g (21.7 mM) of methallyl iodide.

Iodine was recovered 98.6% from the potassium iodide initially used in the form of methallyl iodide. The oil layer was used for the second monoetherification.

(5) Monoetherification by use of the recovered catalyst

To the same reactor as used in the above monoetherification were placed the oil layer of treatment C, 10 g (91 mM) of catechol, 5 g of methyl ethyl ketone and 6.21 g (45 mM) of potassium carbonate, and the air in the reactor was replaced by nitrogen. The mixture was heated to reflux temperature over a period of 10 minutes, and the heating was continued for further 10 hours.

Monoetherification reaction was conducted by repeating treatments A, B and C, and monoetherification. The results were shown in Table 2.

TABLE 2

| No. | Iodine Recovery (%) | Monoether Yield (%) |
|---|---|---|
| 1 | 98.6 | 76 |
| 2 | 99.2 | 74 |
| 3 | 97.9 | 72 |
| 4 | 98.8 | 77 |
| 5 | 98.5 | 75 |

We claim:

1. In the preparation of methallyloxyphenol and recovery and reuse of the iodide component of the catalyst, A. reacting catechol and methallyl chloride in the presence of an alkali iodide catalyst selected from the group consisting of of KI and NaI and mixtures thereof, a base and an organic solvent or a mixture of an organic solvent and water, to provide a reaction mixture containing said alkali iodide catalyst, said base being selected from at least one of carbonates, bicarbonates and hydroxides of alkali metals or alkaline earth metals, cyclic amidines represented by the formula:

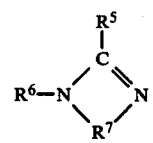

wherein $R^5$ and $R^6$ are each hydrogen or alkyl having 1 to 5 carbon atoms, or joined together to form alkylene having 2 to 11 carbon atoms, and $R^7$ being alkylene having 2 to 6 carbon atoms, and amines represented by the formula:

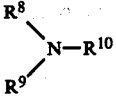

wherein $R^8$ and $R^9$ being each hydrogen, alkyl having 1 to 8 carbon atoms or cycloalkyl having 5 to 8 carbon atoms, or joined together to form alkylene having 5 to 8 carbon atoms, and $R^{10}$ being hydrogen, alkyl having 1 to 8 carbon atoms or phenyl; and said organic solvent is a ketone represented by the formula:

wherein $R^1$ and $R^2$ being each alkyl having 1 to 6 carbon atoms or phenyl, or joined together to form alkylene having 4 to 8 carbon atoms, or aliphatic ester presented by the formula:

wherein $R^3$ being hydrogen or alkyl having 1 to 8 carbon atoms, and $R^4$ being alkyl having 1 to 5 carbon atoms, and B. selectively reacting methallyl chloride with said alkali iodide catalyst in said reaction mixture to produce methallyl iodide for reuse.

2. A process as defined in claim 1 wherein the ketone is acetone, methyl ethyl ketone, methyl isobutyl ketone or cyclohexanone.

3. A process as defined in claim 1 wherein the aliphatic ester is methyl formate, ethyl acetate, amyl propionate, amyl valerate or ethyl pelargonate.

4. A process as defined in claim 1 wherein the carbonate, bicarbonate and hydroxide of alkali metal or alkaline earth metal is $K_2CO_3$, $Na_2CO_3$, $KHCO_3$, $NaHCO_3$, KOH, NaOH, $CaCO_3$, $MgCO_3$, $Ca(OH)_2$ or $Mg(OH)_2$.

5. A process as defined in claim 1 wherein the cyclic amidine is 1,8-diaza-bicyclo[5,4,0]-7-undecene, 1,6-diaza-bicyclo[4,3,0]-5-nonene, 1,5-diaza-bicyclo[4,2,0]-5-octene, 1,4-diaza-bicyclo[3,3,0]-4-octene or 3-methyl-1,4-diaza-bicyclo[3,3,0]-4-octene.

6. A process as defined in claim 1 wherein the amine is methylamine, dimethylamine, trimethylamine, ethylamine, diethylamine, triethylamine, cyclohexylamine, dicyclohexylamine or piperidine.

* * * * *